(12) United States Patent
Chabrier et al.

(10) Patent No.: US 10,463,540 B2
(45) Date of Patent: Nov. 5, 2019

(54) SYSTEM AND DEVICE FOR MULTI SPOT PHOTOCOAGULATION

(71) Applicant: QUANTEL MEDICAL, INC., Cournon-d'Auvergne (FR)

(72) Inventors: Christian Chabrier, La Roche Blanche (FR); Patrice Gayot, Clermont-Ferrand (FR)

(73) Assignee: Quantel Medical, Inc., Cournon-d'Auvergne (FR)

( * ) Notice: Subject to any disclaimer, the term of this patent is extended or adjusted under 35 U.S.C. 154(b) by 257 days.

(21) Appl. No.: 15/107,376

(22) PCT Filed: Dec. 22, 2014

(86) PCT No.: PCT/EP2014/078986
§ 371 (c)(1),
(2) Date: Jun. 22, 2016

(87) PCT Pub. No.: WO2015/097150
PCT Pub. Date: Jul. 2, 2015

(65) Prior Publication Data
US 2017/0000648 A1    Jan. 5, 2017

Related U.S. Application Data

(60) Provisional application No. 61/920,202, filed on Dec. 23, 2013.

(51) Int. Cl.
*A61F 9/00* (2006.01)
*A61F 9/008* (2006.01)
(Continued)

(52) U.S. Cl.
CPC .......... *A61F 9/00821* (2013.01); *A61B 18/20* (2013.01); *A61B 2018/2005* (2013.01);
(Continued)

(58) Field of Classification Search
USPC .............................................. 606/5; 351/205
See application file for complete search history.

(56) References Cited

U.S. PATENT DOCUMENTS 3,984,174 A   10/1976   Landgreen
5,746,738 A   5/1998    Cleary et al.
(Continued)

FOREIGN PATENT DOCUMENTS

EP    2015097150 A2    7/2015
GB    1556046          11/1979
(Continued)

OTHER PUBLICATIONS

International Search Report and Written Opinion for International Application No. PCT/EP2014/078986, dated Jul. 24, 2015 (16 pages).

*Primary Examiner* — Nicole F Lavert
*Assistant Examiner* — Nicole F Johnson
(74) *Attorney, Agent, or Firm* — Kagan Binder, PLLC

(57) ABSTRACT

A photocoagulation system is described herein that facilitates multi-spot laser treatment procedures inside the eye and close to the patient's retina. In one example embodiment, a modified endocular probe operates with a laser system to move the probe or a probe needle so as to project a multi-spot pattern on a patient's retina by controlling the rotation movement of the needle (and needle tip). In addition, the system facilitates maneuverability and angular deviation of the needle tip and synchronizes these different movements with the laser photocoagulator system so as to project the aiming beam and thereafter the laser treatment beam in the desired pattern location with the desired exposure time and power.

14 Claims, 6 Drawing Sheets

(51) Int. Cl.
  *A61B 18/20* (2006.01)
  *A61B 18/22* (2006.01)
(52) U.S. Cl.
  CPC ........... *A61B 2018/2025* (2013.01); *A61B 2018/2211* (2013.01); *A61B 2018/2238* (2013.01); *A61B 2018/2247* (2017.05); *A61B 2018/2253* (2017.05); *A61B 2018/2266* (2013.01); *A61F 2009/00863* (2013.01); *A61F 2009/00897* (2013.01)

(56) References Cited

U.S. PATENT DOCUMENTS

| | | | |
|---|---|---|---|
| 5,921,981 | A | 7/1999 | Bahmanyar et al. |
| 6,096,028 | A | 8/2000 | Bahmanyar et al. |
| 7,566,173 | B2 | 7/2009 | Auld et al. |
| 7,618,177 | B2 | 11/2009 | Cazzini |
| 8,398,240 | B2 | 3/2013 | Smith |
| 8,496,331 | B2 | 7/2013 | Smith |
| 8,951,244 | B2 | 2/2015 | Smith |
| 2007/0027509 | A1* | 2/2007 | Eisenberg ............... A61F 9/008 607/87 |
| 2008/0188910 | A1* | 8/2008 | Spaide ................... A61F 9/008 607/89 |
| 2010/0234834 | A1* | 9/2010 | Mattiuzzi ............... A61B 18/22 606/15 |
| 2013/0110092 | A1 | 5/2013 | Yee et al. |
| 2013/0144278 | A1* | 6/2013 | Papac ................. A61F 9/00821 606/4 |

FOREIGN PATENT DOCUMENTS

| | | |
|---|---|---|
| WO | 9314430 A1 | 7/1993 |
| WO | 2007076533 A2 | 7/2007 |
| WO | 2007112030 A2 | 10/2007 |
| WO | 2008024848 A2 | 2/2008 |
| WO | 2011037651 A1 | 3/2011 |

* cited by examiner

SYSTEM AND DEVICE FOR MULTI SPOT PHOTOCOAGULATION

CROSS-REFERENCE TO RELATED APPLICATIONS

This application claims the benefit of International Application No. PCT/EP2014/078986filed Dec. 22, 2014, and titled "SYSTEM AND DEVICE FOR MULTI SPOT PHOTOCOAGULATION", which in turn claims priority from U.S. Provisional Patent Application No. 61/920,202, filed Dec. 23, 2013 and titled "SYSTEM AND DEVICE FOR MULTI SPOT PHOTOCOAGULATION" both of which are incorporated herein by reference in their entireties.

FIELD AND BACKGROUND OF THE INVENTION

This invention relates to laser ophthalmic surgery and more particularly to a method and system particularly suited to for photocoagulation procedures performed on a human patient.

Photocoagulation has been used for various ophthalmic procedures with such procedures being performed using either a slit-lamp (SL) laser delivery system or, when surgical intervention is required, endocular laser probes. In the slit-lamp system, laser energy is delivered from the laser source to the imaging optics via a single optical fiber and the procedure can be relatively fast and with good quality results. As is known, the imaging optics is used in conjunction with a variety of contact lenses, and must be capable of focusing the output end (distal) of the fiber onto the retina. The focal length of the imaging optics, is typically variable, i.e. zoom, to magnify the size of the fiber's image on the retina from 1 to 20 times, corresponding to 50-1000 microns on the retina. Current SL systems offer a single fiber for single point exposure on the surgical area. The surgeon positions the fiber image to the desired location by observing a low energy aiming beam on the treatment area. By turning the laser on/off and moving the aiming beam, the surgeon can lay down a pattern of spots on the treatment area. The number of spots is determined by the size of the treatment area and the laser spot size desired. For photocoagulation of micro aneurysms on the retina, the laser spot size should be small (<100 microns) to avoid damage to surrounding tissue.

The time to position the spot and deliver the laser energy depends on the features of the SL and the skill of the surgeon and is typically 1 second per spot. This means that the treatment time is in excess of 30 minutes which is fatiguing to the patient and surgeon. Also, laying down a uniform pattern is difficult and the pattern is typically more random than geometric in distribution. When the treatment requires surgical intervention, the SL is not used and instead a standard endocular laser probes are utilized. The treatment objectives are the same, however, to lay down a pattern of photocoagulative burns in the affected area using the endolaser (or endocular) probe, the surgeon holds the distal tip close to the retina and lays down 1500-2000 spots, 500 microns in diameter. This procedure can take more than half an hour and using the probe close to the retina may increase the risk of accidental tears with the length of the procedure tending to prolong the anesthesia time in high risk patient groups.

Therefore there is a need for a system that provides the quality and speed of slit lamps systems in an endocular probe oriented procedure.

SUMMARY OF THE INVENTION

The various embodiments of the photocoagulation system described herein allow performing multi-spot laser treatment procedures inside the eye and close to the retina. In one example embodiment, a modified endocular probe operates with a laser system to move the probe or a probe needle so as to project a multi-spot pattern on a patient's retina by controlling the rotation movement of the needle (and needle tip). In addition, the system facilitates maneuverability and angular deviation of the needle tip and synchronizes these different movements with the laser photocoagulator system so as to project the aiming beam and thereafter the laser treatment beam in the desired pattern location with the desired exposure time and power. In this and various example embodiments, the photocoagulator uses wavelengths from about 514 nm to about 815 nm, and preferably in the range of, but not limited to, about 532 nm to about 577 nm.

Unlike prior art methods of using the endocular probe to perform a spot by spot pattern and treatment, the systems described herein are capable of generating numerous multi-spot patterns by transforming one spot into several spots using an optic member with at least one optical fiber that is divided into several spots at the fiber or probe's output or with several/multiple fibers mixed together to deliver the pattern (alignment or treatment). One of the advantages of the teachings herein is the ability to generate patterns with mechanical (translation or rotation or angular) movement of an endocular probe or its needle (and needle tip).

In another example embodiment, a photocoagulator system includes a standard ophthalmologic photocoagulator laser configured to facilitate synchronization with a probe holder handle or device. The system further includes a specially configured probe holder device adapted to hold an endocular probe and permit the control of the movement of this probe or/and its needle and eventually of a needle tip. The system also includes a specially configured endocular probe having a fixed angle shaft or needle tip or, alternatively, a needle probe with an angle adjustable tip that operates within the holder device housing. This system will facilitate multi-spot treatment within the retina using only a fixed angle tip endocular probe that can now form simple patterns, such as 4 spot square or multi-spot circle by tracing only a single circular movement (discussed and illustrate further below). In a related embodiment, using an endocular probe with an angle adjustable tip, by tracing or forming several circles or circular movement with circles of different diameters (and in concentric circle arrangements, in one example), the user can generate complex patterns such as a large square, one or two circles or using the sub-patterns to fill in a larger sector or area (as illustrated later in the application).

In a related embodiment, the photocoagulator laser is configured with an output plug adapted to drive the probe holder via a cable having electrical, electronic and communications capabilities. Synchronize the movement of the probe laser tip (rotation and angle deviation) and the delivery of the laser aiming and treatment beam. Ensure the safety of the position detection of the probe laser tip in case of problem. We will add also particular software to permit to the user to choose the desired pattern and to control all the process In one example embodiment, an endocular probe with an angularly movable tip is provided that a user can hold and fix the probe in a desired position. In addition, the probe and/or the needle tip can be driven and controlled in a rotational movement by a motor. The desired angular positions for the probe or the needle are received from the laser system, which controls the precise positioning rotation with the use of a sensor to regulate/monitor the angular rotation position and which can stop the rotation at a desired location or position, spot by desired spot location. The laser system can also synchronize these probe/needle positions so as to deliver the alignment or treatment beam only at the desired location. To ensure position control safety and to stop the treatment laser if the location or positions of the probe or needle tip is not the desired or correct one. With certain endocular probes with angle adjustable tips, the laser system is configured to hold and fix in a certain position the probe or to drive and control rotation movement of the probe or the needle via a separate motor. In a related embodiment, movement, rotation, longitudinal translation, etc. of the probe and/or needle (or tip) are controlled through a motor using an actuator or push button.

In related embodiments, a probe holder housing is configurable to facilitate similar movements described herein. The probe holder is configurable to fix the probe in a desired position or to transmit instructions for the rotation movement of the probe or of the needle itself via a motor in the handle piece holder. Using an actuator as part of the probe holder assembly, commands are transmitted to facilitate angle deviation or movement of the needle tip by the motor in the handle piece holder. In a related embodiment, mechanical and/or electrical features added to endocular probe permit checking the positioning of rotation of the probe or needle or needle tip. The motor and sensor also ensure that the needle remains fixed and avoid any movement (rotational or otherwise).

In one example embodiment, a photocoagulator laser system includes a system controller and a laser source for generating an aiming beam and a treatment beam, the system comprising: a probe having a distal end and a proximal end, the proximal end being coupled to a fiber optic cable that is coupled to the laser source, the distal end of the probe configured for ophthalmologic procedures and configured to have a longitudinal portion and an angled tip at the end of the longitudinal portion. In this example embodiment, the distal end of the probe is configured to angularly rotate thereby forming at least one circle with spots located thereon that form alignment pattern and/or a treatment pattern of spots. The system further includes a probe holder adapted to hold the probe and configured to operatively communicate with the system controller. In one example embodiment, the system includes a probe holder, which includes a motor for longitudinal displacement of the probe; a probe displacement sensor; and a control circuit member operatively coupled to the displacement motor and the displacement sensor and adapted to communicate with the system controller. In this embodiment, the displacement motor is adapted to engage an actuator operatively coupled to the probe and configured to control longitudinal displacement of the probe, and wherein the displacement sensor is adapted to sense a displacement member located on the probe and configured to communicate displacement movement of the probe.

In a related example embodiment, the probe holder further includes a motor for angular rotation of the probe; a probe angular rotation sensor; and a control circuit member operatively coupled to the angular rotation motor and the angular rotation sensor and adapted to communicate with the system controller. In this example embodiment, the angular rotation motor is adapted to engage an actuator operatively coupled to the probe and configured to control angular rotation or displacement of the probe, and wherein the angular rotation sensor is adapted to sense an angular rotation member located on the probe and configured to communicate angular rotation movement of the probe.

In another example embodiment, there is provided a laser or endocular probe assembly including a housing, a motor for longitudinal displacement of an endocular probe, a probe displacement sensor, and a control circuit member operatively coupled to the displacement motor and the displacement sensor and adapted to control the motor and the sensor. In this example embodiment, the displacement motor is adapted to engage an actuator operatively coupled to the probe and configured to control angle displacement of the probe through a longitudinal movement, and wherein the displacement sensor is adapted to sense a displacement member located on the probe and configured to communicate angle displacement movement of the probe or probe tip to the control circuit member.

The invention now will be described more fully hereinafter with reference to the accompanying drawings, which are intended to be read in conjunction with both this summary, the detailed description and any preferred and/or particular embodiments discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

BRIEF DESCRIPTION OF THE DRAWINGS

Other important objects and advantages of the present invention will be apparent from the following detailed description of the invention taken in connection with the accompanying drawings in which.

DETAILED DESCRIPTION OF THE INVENTION

Following below are more detailed descriptions of various related concepts related to, and embodiments of, methods and apparatus according to the present disclosure for an improved diagnostic and treatment system that speeds up eye treatment time while improving accuracy and reliability of the selected treatment by the physician. It should be appreciated that various aspects of the subject matter introduced above and discussed in greater detail below may be implemented in any of numerous ways, as the subject matter is not limited to any particular manner of implementation. Examples of particular implementations and applications are provided primarily for illustrative purposes.

Figure 1:
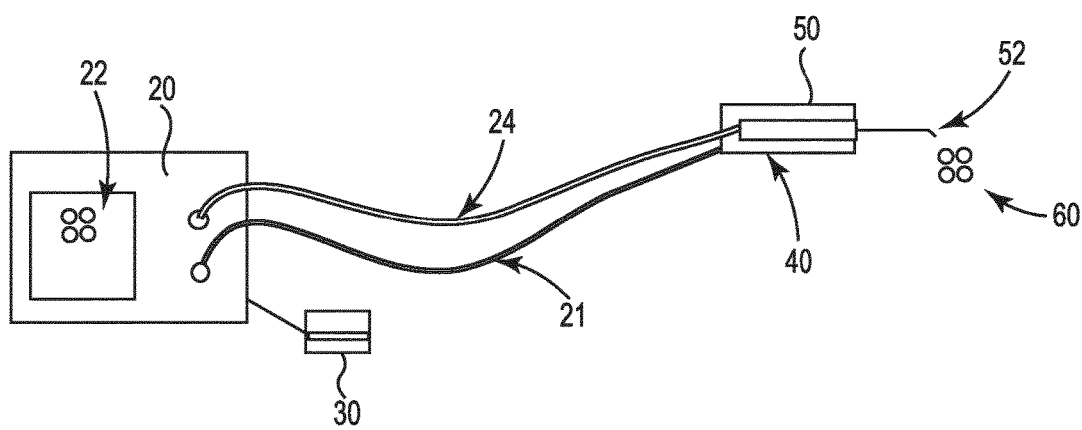
FIG. 1 is a multispot surgical laser system in accordance with the invention.

Referring now to the Figures, FIG. 1 is a multispot surgical laser system 10 in accordance with the invention.

System 10 includes laser photocoagulator 20 coupled to a footswitch 30, which controls at firing mode and a slit lamp (among other items associated with the photocoagulator), and having an electrical cord or cable 21 to power the system and in some embodiments to use for control or communication as well. Photocoagulator 20 includes a screen or display 22 to permit the user or physician to choose a desired alignment and/or treatment pattern and to control all the other treatment parameters such as, but not limited to, the power of the treatment beam and exposure time. An optical fiber 24 is operatively coupled to photocoagulator 20 on one end and to a handheld member or holder 40 on the other end. In this example embodiment, fiber 24 is operatively coupled to an endocular probe 50, which may be housed within probe holder 40, which has a needle 52 and needle tip 52A coupled thereto. In this example embodiment, needle tip 52 projects therefrom an alignment pattern 60 (and when actuated a treatment pattern that overlays the alignment pattern) on a patient's retina. The patterns that are configurable and generated by this system are discussed herein.

Figure 2A:
FIGS. 2A-2G are various alignment and treatment patterns configurable by the various systems disclosed herein.
Figure 2B:
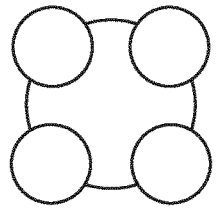
Figure 2C:
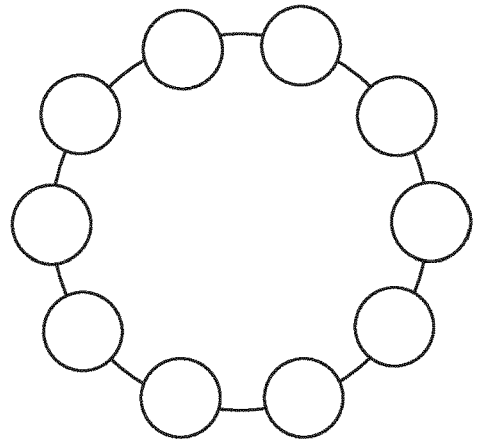

Referring now to FIGS. 2A-2G are various alignment and treatment patterns configurable by system 10 and various other laser systems disclosed herein. Examples of possible patterns that can be generated from the systems taught herein include (of different sizes) a square, a circle, rectangle, a line, a define sector or area filled in with several spots by doing one or several turns of a particular modified endocular fiber 24 or needle 52 inside handle piece holder 40. This is accomplished by synchronization between laser 20 and endocular fiber needle 52 resulting in turning or rotating needle tip 52A as well as creating an angle deviation at the needle tip (thereby projecting movement at the needle tip). The spot diameter on the retina will vary with the distance between endocular fiber tip and target tissue. FIG. 2A illustrates a single spot generated with a standard endocular fiber. FIG. 2B illustrates, on the other hand, a four spot pattern (small square) generated with system 10 and probe 50, with one turn (or rotation) of a coupled or connected fixed angle endocular probe or, alternatively, a particular endocular probe with tip angle that is adjustable. FIG. 2C illustrates an example of a circular pattern with 10 spots generated with about one turn of a coupled fixed angle endocular probe or a coupled endocular probe with an adjustable tip angle.

Figure 2D:
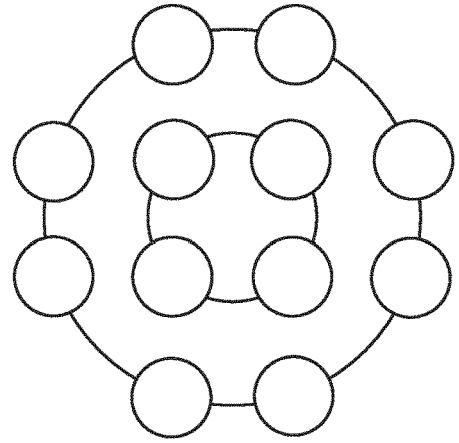
Figure 2E:
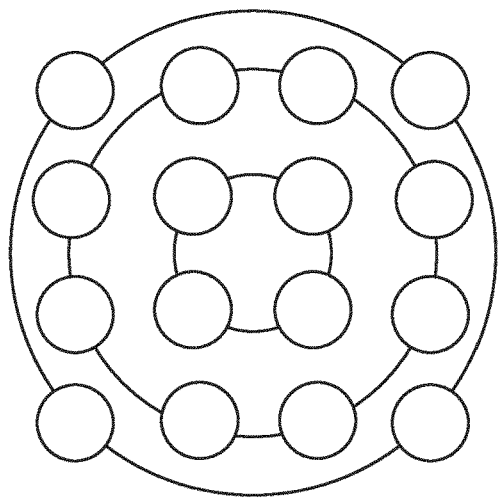
Figure 2F:
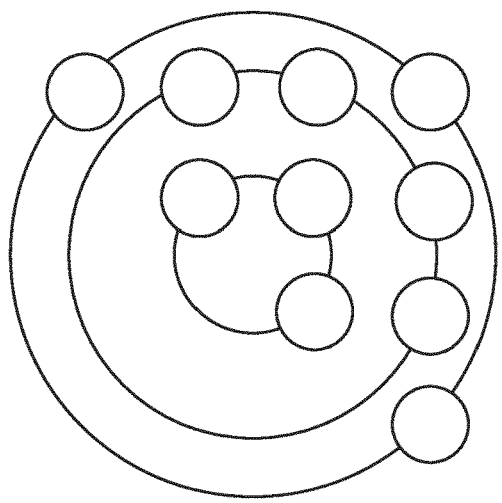
Figure 2G:
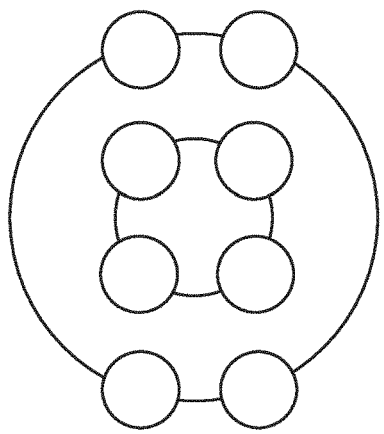

In FIG. 2D there is illustrated an example of a 12 spot pattern generated with about two turns or rotations of a coupled endocular probe with an adjustable tip angle. FIG. 2E illustrates an example of a 16 spot pattern (resulting in a 4×4 square pattern) generated with about three turns of a coupled endocular probe with an adjustable tip angle. FIG. 2F illustrates yet another example of a 10 spot sector pattern, similar to an arc pattern, generated with about three turns of a coupled endocular probe with an adjustable tip angle. FIG. 2G illustrates yet another example of an 8 spot rectangular pattern generated with about two turns of a coupled endocular probe with an adjustable tip angle. Hence, it is apparent to one skilled in the art that numerous patterns and sector filling schemes are possible with the laser system taught herein.

Figure 3:
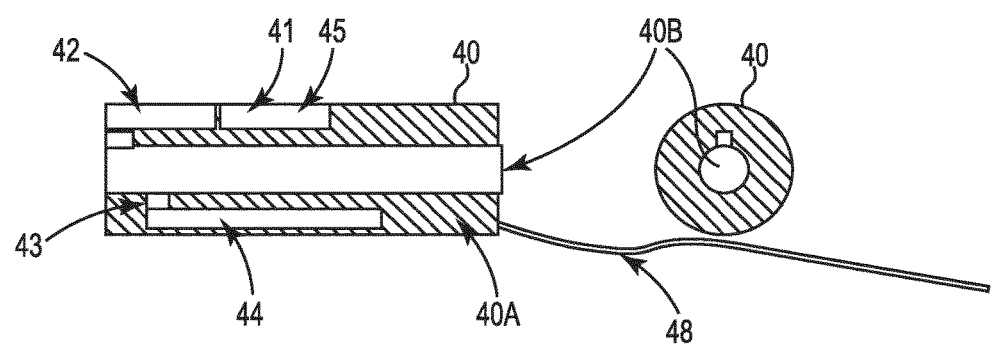
FIG. 3 illustrate probe handle holder in accordance with the invention.
Figure 4:
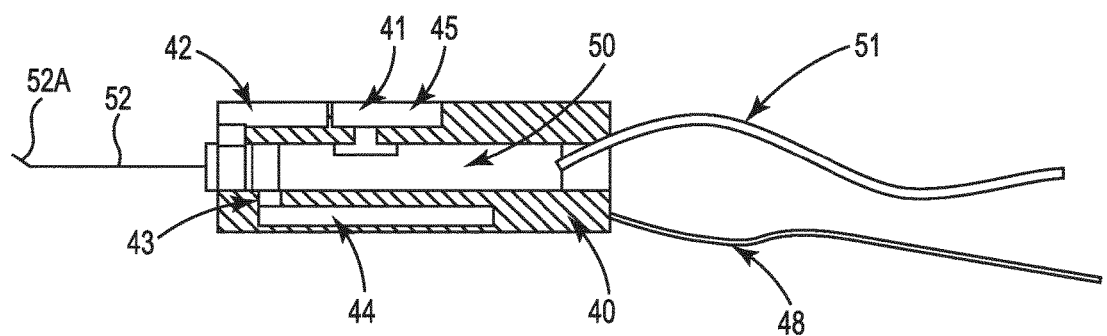
FIG. 4 illustrate probe handle holder with an endocular probe inserted in accordance with the invention.

Referring now to FIGS. 3 and 4, there is illustrated an example embodiment of probe handle holder 40 that includes a probe housing 40A and a probe cylindrical opening 40B that spans along a length of housing 40A, opening 40B configured to accept an endocular probe 50, with an optical fiber 51 being coupled to probe 50. Probe housing 40A includes therein a motor 41 adapted to drive an angle of probe or the tip of needle 52 and includes a sensor 45 adapted to check the angle of probe 50 or the angle of needle tip 52A indirectly. In this example embodiment, probe housing 40A further includes a motor 42 to rotate needle 52 or probe 50 (depending on the desired embodiment) and a sensor 43 to check the angle of rotation of the probe or needle. Housing 40A also includes a circuit board 44 which includes circuitry and processors that control the various motors in the probe housing to generate the desired probe position (angular rotation and/or displacement) or needle tip angle position 52A. In a related embodiment, board 44 is configured to communicate with a photocoagulator system controller. An electrical cord or cable 48 is coupled to housing 40 on one end and is operatively coupled to laser 20 at the other end and establishes synchronization for movement of the probe tip position angularly and rotationally. In this example embodiment, the longitudinal movement controls how much angle there will be in needle tip 52A. Changing the needle tip 52A angle corresponds directly to the size of the circle to be made within the retina to assist in forming the various aiming beam patterns. In a related embodiment, the probe holder and motors control the longitudinal movement or displacement (or in/out of the holder) of the probe and needle.

Figure 5A:
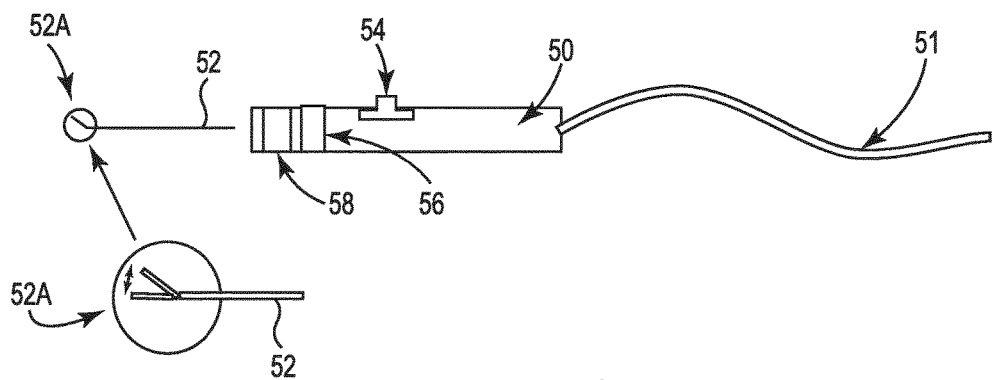
FIGS. 5A-5B illustrate endocular probes which can fit inside the probe holder in accordance with the invention.
Figure 5B:
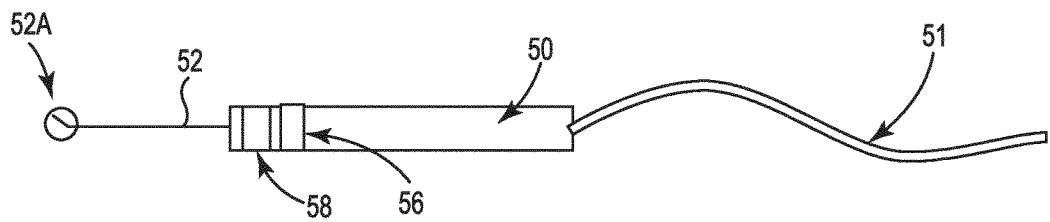

Referring now to FIGS. 5A-5B are two example embodiments of endocular probes 50 in accordance with the invention. In FIG. 5A, probe 50 is coupled to fiber 51, while fiber 51 is optically and/or electrically coupled to laser 20. A button actuator 54 is included that is operatively coupled to probe 50 so as to facilitate one or more of the following: mechanical push/pull or movement/translation longitudinally along probe housing 40A length (in and out of housing 40A) and within cylinder 40B; with rotational movement capability to permit movement of the probe body or of needle tip 52 in various angles 52A of the endocular probe. Button or actuator 54 can also be configured to allow device sensor 43 to verify or determine endocular probe tip angle 52A. Displacement member 56 located on probe 50 is configured to permit the device sensor 43 to determine each of the endocular probe and needle position in terms of angular rotation. Angular rotation member 58 located on probe 50 is configured to (mechanically or otherwise) fix or hold the probe holder so as to permit angular turning or rotating of the probe 50 or needle 52. The inset figures illustrate movement of (in various angles) needle tip 52 in response to actuator 54.

Figure 6:
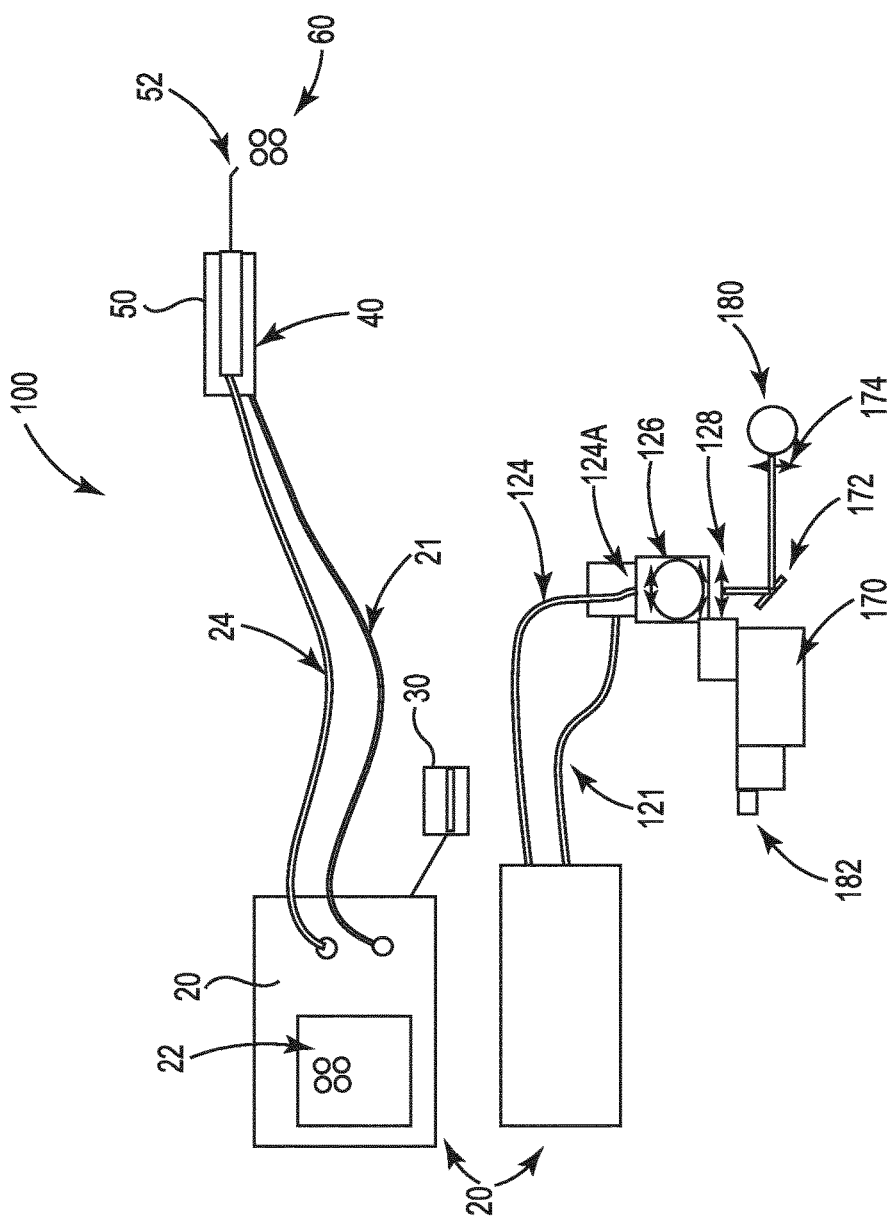
FIG. 6 is another multispot surgical laser system in accordance with the invention.

Referring now FIG. 6, there provided another multispot surgical laser 100 system with some similar elements as in system 10 except those elements are adapted to provide slit lamp type ophthalmology treatments as taught herein. In this example embodiment, electrical cord 121 and optic fiber 124 are coupled to laser source 20 with the other end of fiber tip 124A coupled to a device so as to permit translational/deviation movement as well as rotation of the tip using motors (not shown) and position sensors. Such device is then coupled to a fixed spot size changer 126 which is also coupled to a focus lens 128. A patient's eye 180 is diagnosed and treated by a user 182 using a slit lamp 170 which is able to control a mirror with a micromanipulator 172 that reflects light from tip 124A through a contact lens 174 to the patient's eye 180. Modifications known to one skilled in the art can be made to system 100 so as to project and treat several various patterns on the patient's eye, including the retina and cornea. The patterns illustrated in FIG. 2A-2G, which are generated by systems 10 and 100, are displayable to the user in display 22 to ensure the correct treatment pattern is being used otherwise adjustments can be made.

The aforementioned teachings are also applicable to slip lamp systems where alignment and treatment patterns can be formed by rotational and translational movement of the fiber without the use of a scanner which deviates or moves the laser beam as opposed to the fiber or probe as described herein. In addition, where zoom is not needed for adjusting spot size we can use only one fixed spot size or several fixed spot sizes and form standard patterns using this invention to fill in a sector or area to be treated.

The following patents and publications that relate to ophthalmology diagnostic and treatment systems are herein incorporated by reference in their entirety and constitute part of the disclosure herein: U.S. Patent and Publication Nos. U.S. Pat. Nos. 6,096,028; 8,496,331; U.S. 2011/0144627; and WO 2008/024848 A2.

The foregoing particular embodiments of the invention as set forth herein are for illustrative purposes only. Various deviations and modifications may be made within the spirit and scope of the invention without departing from the main theme thereof.

What is claimed is:

1. A photocoagulation system including a system controller and a laser source for generating an aiming beam and a treatment beam, the system comprising:
   a probe having a distal end and a proximal end, the proximal end being coupled to a fiber optic cable that is coupled to the laser source, the distal end of the probe configured for ophthalmologic procedures, wherein the distal end of the probe includes a longitudinal portion and an angled probe tip at the end of the longitudinal portion;
   wherein the angled probe tip of the distal end of the probe forms a directional angle relative to the longitudinal portion of the distal end of the probe, wherein the distal end of the probe is a needle and the angled probe tip is a needle tip that includes a configurable directional angle relative to a longitudinal portion of the needle that is either fixed or variable;
   wherein the needle including the needle tip is configured to angularly rotate thereby forming at least one circle with spots located thereon that form alignment pattern and/or a treatment pattern of spots.

2. The system of claim 1, wherein the distal end of the probe is configured to form a plurality of concentric circles with a plurality of spots, thereby forming the desired alignment and treatment pattern.

3. The system of claim 2, further comprising a probe holder adapted to hold the probe and configured to operatively communicate with the system controller.

4. The system of claim 3, wherein the probe holder further comprises:
   a motor for longitudinal displacement of the probe;
   a probe displacement sensor; and
   a control circuit member operatively coupled to the displacement motor and the displacement sensor and adapted to communicate with the system controller;
   wherein the displacement motor is adapted to engage an actuator operatively coupled to the probe and configured to control longitudinal displacement of the probe, and wherein the displacement sensor is adapted to sense a displacement member located on the probe and configured to communicate displacement movement of the probe.

5. The system of claim 3, wherein the probe holder further comprises:
   a motor for angular rotation of the probe;
   a probe angular rotation sensor; and
   a control circuit member operatively coupled to the angular rotation motor and the angular rotation sensor and adapted to communicate with the system controller;
   wherein the angular rotation motor is adapted to engage an actuator operatively coupled to the probe and configured to control angular rotation or displacement of the probe, and wherein the angular rotation sensor is adapted to sense an angular rotation member located on the probe and configured to communicate angular rotation movement of the probe.

6. The system of claim 4, wherein the needle and needle tip being responsive to at least one of the actuator, the displacement motor and the angular rotation motor.

7. The system of claim 3, wherein the aiming beam is generated inside the probe holder.

8. The system of claims 4, wherein the displacement motor and the angular motor are configured from mechanical components and springs that provide similar displacement and rotational movement of the probe.

9. The system according to claim 2, wherein the probe includes an optical element at the needle tip to deviate a laser beam on a side with an angle.

10. The system according to claim 2, wherein the probe includes a specific cut or shape at the needle tip to deviate the laser beam on the side with an angle.

11. The system according to claim 2, wherein the optical probe includes a focusing element or a ball lens at the needle tip.

12. The system according to claim 2, wherein the probe includes at least one of a fiber with illumination, a fiber with a tapered end and a fiber with a coated or treated or shaped end.

13. The system according to claim 2, wherein the optical probe includes multiple optical fibers arranged in a geometric relationship at the proximal end of the probe.

14. The system according to claim 1, wherein the probe includes at the needle tip an optical element that includes a diffractive optic that divides the alignment and/or treatment beam into multiple beams.

* * * * *